(12) United States Patent
Howell et al.

(10) Patent No.: US 6,740,277 B2
(45) Date of Patent: May 25, 2004

(54) PROCESS OF MAKING A CATHETER

(75) Inventors: Glade Harold Howell, Sandy, UT (US); Cynthia Anne Castro, Sandy, UT (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 85 days.

(21) Appl. No.: 10/131,365

(22) Filed: Apr. 24, 2002

(65) Prior Publication Data

US 2003/0204169 A1 Oct. 30, 2003

(51) Int. Cl.[7] .......................... B29C 47/20; B29C 71/02
(52) U.S. Cl. ................ 264/209.3; 264/236; 264/320; 264/338
(58) Field of Search .................... 264/209.3, 236, 264/320, 338

(56) References Cited

U.S. PATENT DOCUMENTS

| | | | |
|---|---|---|---|
| 4,588,398 A | 5/1986 | Daugherty et al. | 604/265 |
| 4,661,300 A | 4/1987 | Daugherty | 264/40.6 |
| 5,120,317 A | 6/1992 | Luther | |
| 5,531,701 A | 7/1996 | Luther | |
| 5,533,988 A | 7/1996 | Dickerson et al. | |
| 5,589,120 A | 12/1996 | Khan et al. | 264/130 |
| 5,593,718 A | 1/1997 | Conway et al. | 427/2.3 |
| 5,683,370 A | 11/1997 | Luther et al. | 604/282 |
| 5,736,085 A | 4/1998 | Brown et al. | 264/161 |
| 5,792,401 A | 8/1998 | Burnham | 264/103 |
| 5,843,356 A | 12/1998 | Patel et al. | 264/161 |
| 5,919,164 A | 7/1999 | Andersen | 604/102 |
| 5,971,954 A | 10/1999 | Conway et al. | 604/96 |
| 6,012,213 A | 1/2000 | Chang et al. | 29/447 |
| 6,013,190 A | 1/2000 | Berg et al. | 216/34 |
| 6,030,371 A | 2/2000 | Pursley | 604/282 |
| 6,045,734 A | 4/2000 | Luther et al. | 264/103 |
| 6,187,130 B1 | 2/2001 | Berard et al. | 156/294 |
| 6,280,788 B1 | 8/2001 | Rakhorst et al. | 427/2.1 |

FOREIGN PATENT DOCUMENTS

JP  P2001-149483 A  6/2001

*Primary Examiner*—Leo B. Tentoni
(74) *Attorney, Agent, or Firm*—James J. Murtha (57) ABSTRACT

An over-the-needle catheter assembly includes a tube made of a flexible, biocompatible material. The tube has a proximal portion, a distal portion and a catheter tip positioned on the distal portion remote from the proximal portion. A lumen extends through the tube, substantially co-axially with the tube, from the proximal portion, through the distal portion and through to the catheter tip. The lumen cross-section at the proximal portion is larger than the cross-section at the distal portion. A shoulder is disposed in the lumen between the distal portion and the proximate portion. A catheter land, having a predetermined length, is defined as the portion of the lumen disposed in the distal portion of the tube between the shoulder and the distal end. A needle is disposed in the lumen and has a substantially circular cross-section. A discontinuity is located on the needle at a predetermined position with respect to the needle tip. The distance between the distal edge of the discontinuity and the needle tip is substantially equal to the length of the catheter land. The discontinuity is sized such that it fits within the lumen at the proximal portion but does not fit within the lumen at the distal portion.

25 Claims, 10 Drawing Sheets

PROCESS OF MAKING A CATHETER

FIELD OF THE INVENTION

This invention relates to the field of medical devices for the introduction and removal of fluids from a patient. More particularly, the invention relates to catheters and a method of manufacturing catheters for use with a needle.

BACKGROUND OF THE INVENTION

Medical devices, such as intravenous (IV) catheters, have been developed for insertion into the tissues of a body cavity of a patient to introduce or remove fluids. Such devices are most commonly intended for intravascular use, particularly for infusion of normal intravenous solutions, including antibiotics and other drugs, although various other uses are quite common. IV catheters are also used to withdraw blood from the patient for normal blood-gas analysis as well as other blood work. While IV catheters are available in several different types, one common type of catheter is constructed so as to be mounted coaxially upon a relatively long, hollow needle or cannula with a slight friction fit, referred to herein as an "over-the-needle" arrangement. A hub is attached at one end of the catheter and is designed so as to be connectable with and detachable from an IV fluid supply line. To insert the catheter into the patient, the needle and catheter together are inserted through the patient's skin, whereupon the needle may be withdrawn, leaving the catheter in place.

Since the catheter will normally be left in position for at least several hours, it must be flexible and efficiently shaped for the introduction of fluid or removal of fluid. The shape of the catheter tip must produce minimal trauma to the patient during insertion of the catheter into the patient and while the catheter is in place in the patient. A tip shape that provides these characteristics has a tapered outer wall and an angled tip and is disclosed in U.S. Pat. No. 4,588,398, incorporated herein by reference. A process for making such a catheter tip is disclosed in U.S. Pat. No. 4,661,300, incorporated herein by reference. In this process, the catheter is placed on a mandrel. A die having an interior molding surface, which is tapered according to the tip desired on the catheter, is aligned axially with the mandrel. The die is heated, typically using RF energy, thereby heating the catheter tip so that it becomes flowable. The mandrel and die are brought together so the distal edge of the mandrel engages the tapered portion of the die. This action cleanly forms a smooth and uniform tapered tip for the catheter but has not been designed specifically to address formation of the internal geometry of the catheter and is incapable of achieving the preferred geometry of the instant invention.

Catheters must be designed of materials and to have shapes that are rigid enough to pass through the tissue of the patient and yet soft enough to avoid discomfort and tissue trauma to the patient when in place. During insertion, the forces exerted on the flexible catheter by the patient's tissue may cause a "peeling back" of the catheter, preventing the catheter from full insertion into the patient's vein. This problem can be compounded when the needle and catheter must be inserted into a septum of an implantable infusion port (such ports may be implanted in a patient for long term vascular access). These ports may provide a higher resistive force than human tissue. Consequently, the catheter, particularly its tip, must include some structural rigidity.

Concerns for safety have driven the development of devices that capture the tip of a needle within a container of some sort. See, e.g., U.S. Pat. No. 6,004,294 and U.S. application Ser. No. 09/717,148, filed Nov. 21, 2000, both incorporated herein by reference. In certain such systems, it is advantageous to have a discontinuity, such as a bump or annular ring, on the needle, near the tip, to be grasped and held by the closed container (preventing the needle from exiting the container). However, prior art systems for forming catheters may result in inconsistent internal catheter geometry that interferes with the insertion of the needle into the catheter. Consequently, the tip of the needle cannot always be positioned at a specific desired location beyond the tip of the catheter. Further, even if positioned correctly, the inconsistent formation of catheters may result in an inconsistent (and thus undesirable) force to remove the needle from the catheter once in position.

SUMMARY OF THE INVENTION

It is therefore an advantage of an aspect of this invention to provide a catheter and a method of making catheters that can be efficiently inserted into patients, including into septums implanted within patients, with minimal patient discomfort and left in patients while minimizing any vascular trauma.

It is an advantage of another aspect of the invention to provide a catheter and a method of making a catheter that can be employed consistently with a needle having a discontinuity near the needle tip.

It is an advantage of yet another aspect of the invention to provide a catheter and a method of making a catheter that can be inserted into a patient's tissue or a septum without pealing back off the needle.

The above and other advantages and objects of the invention will be apparent upon consideration of the following description.

In accord with one aspect of the invention, a method is provided for forming a catheter for insertion into a patient's skin. A flexible, biocompatible material is extruded into a tube. The tube has an inner wall defining a substantially constant inner cross-section, an outer wall defining a substantially constant outer cross-section and an axis. A lumen is defined by the inner wall and extends co-axially within the tube from a proximal portion, through a distal portion to a distal face, forming an opening in the distal face of the tube. A mandrel is provided that has a body portion and a tip portion. The body portion has a larger cross-section than the tip portion. Typically, the body portion has a cross-section that is the same as or less than the inner cross-section of the tube. The mandrel is inserted into the lumen such that the tip portion of the mandrel is disposed in the distal portion of the tube proximate to the distal face of the tube. The distal portion of the tube is deformed such that the outer wall tapers inward toward the opening and the inner wall conforms to the tip portion of the mandrel. The portion of the tube's inner wall that has conformed to the tip portion of the mandrel defines a catheter land having a predetermined cross-section substantially matching the cross-section of the tip portion and a predetermined length. The catheter is cured and the mandrel is withdrawn from the lumen.

Certain implementations of this aspect of the invention provide that the material of the tube is thermoplastic and is deformed by heating in a hot die. Other plastic materials may be employed and may be formed as necessary, including any required curing steps, to achieve the desired geometry. The mandrel may be positioned so that the free end of the mandrel is co-located with the distal opening in the tube, or so that the free end extends through the distal opening. The tip portion of the mandrel may have various shapes to impart a desired geometry to the catheter land, such as grooves to form ridges in the land, or a conical shape to form a conical land. Such ridges may be employed to direct the tearing of a catheter when use as a splittable introducer, such as disclosed in U.S. Pat. Nos. 6,080,141, 6,027,480 and 6,273,871, each incorporated herein by reference. The needle itself may be used as the mandrel, and may be heated to assist forming the catheter.

In accord with another aspect of the invention, an over-the-needle catheter assembly is provided including a tube made of a flexible, biocompatible material. The tube has a proximal portion, a distal portion and a catheter tip positioned on the distal portion remote from the proximal portion. A lumen extends through the tube, substantially co-axially with the tube, from the proximal portion, through the distal portion and through to the catheter tip. The lumen has a proximal cross-section in the proximal portion of the tube and a distal cross-section in the distal portion of the tube. The proximal cross-section is larger than the distal cross-section. A shoulder is disposed in the tube between the distal portion and the proximal portion. A catheter land, having a predetermined length, is defined as the portion of the lumen disposed in the distal portion of the tube between the shoulder and the distal end. A needle is disposed in the lumen and has a substantially circular cross-section. A discontinuity is located on the needle at a predetermined position with respect to the needle tip. The distance between the distal edge of the discontinuity and the needle tip is substantially equal to the length of the catheter land. The discontinuity is sized such that it fits within the lumen at the proximal portion but does not fit within the lumen at the distal portion.

Certain implementations of this aspect of the invention provide that the shoulder is disposed at a selected angle with respect to the axis of the lumen.

DETAILED DESCRIPTION OF THE INVENTION

Figure 2:
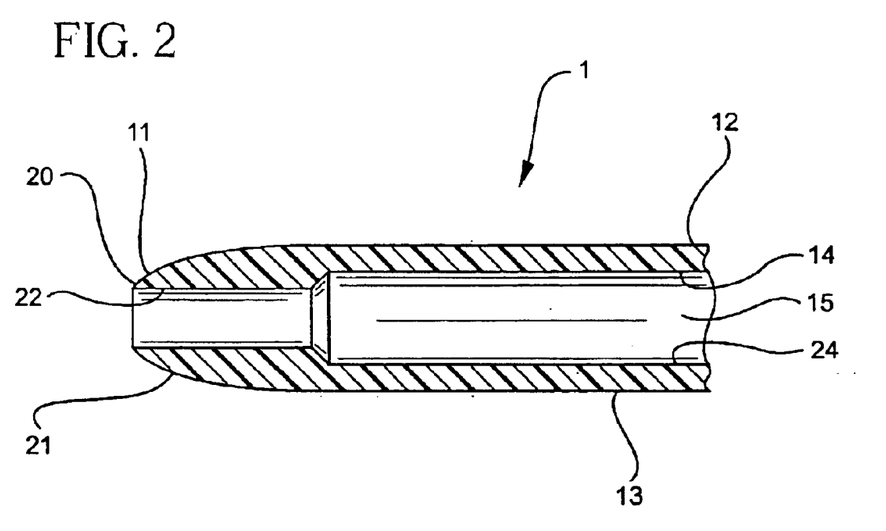
FIG. 2 is a cut-away view of a catheter made in accord with an aspect of the instant invention.
Figure 3:
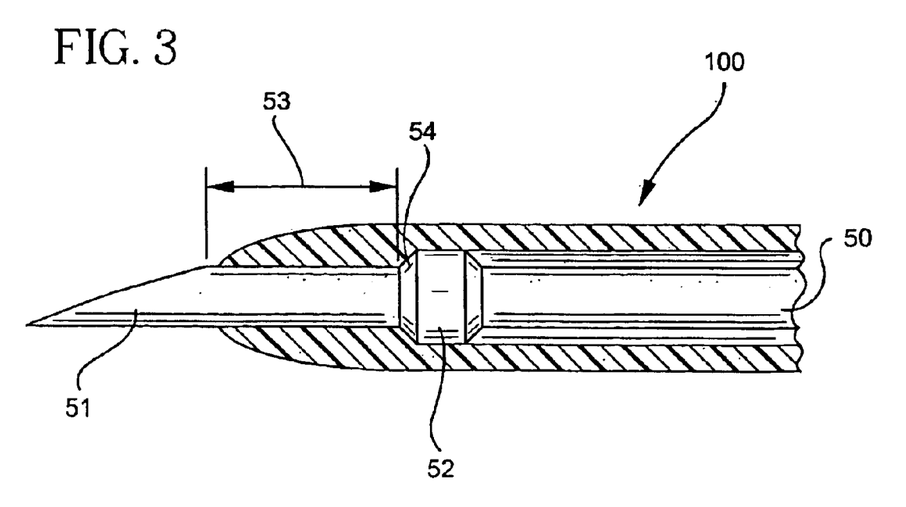
FIG. 3 is a cut-away view of the catheter of FIG. 2 shown mounted on a needle, forming an over-the-needle catheter assembly.

As used herein, the term "proximal" refers to a location on the catheter and introducer needle assembly that, during normal use, is closest to the clinician using the device and farthest from the patient in connection with whom the device is used (the left side of FIGS. 2 and 3). Conversely, the term "distal" refers to a location on the catheter and introducer needle assembly that, during normal use, is farthest from the clinician using the device and closest to the patient in connection with whom the device is used (the right side in FIGS. 2 and 3).

Referring to the figures, an aspect of the instant invention is related to flexible catheters 1 for use in connection with an over-the-needle catheter assembly 100 and their manufacture. The catheter 1 formed in accord with the instant invention includes a distal portion 11 and a proximal portion 12. The catheter includes an outer wall 13 and an inner wall 14, with a central lumen 15 extending axially therein and defining a fluid flow path from the tip 20 of the catheter through to the proximal end of the catheter. The tip 20 of the catheter is shaped to form a beveled surface 21, such as disclosed in U.S. Pat. No. 4,588,398 incorporated herein by reference. The beveled surface is designed to smoothly pass through the patient's tissue and to cause minimal discomfort and abrasion while positioned within the tissue. Of course, the tip may have other shapes and still practice aspects of the invention.

A needle 50 is typically made of stainless steel and includes a central axial cavity extending completely through the needle to the needle tip 51. The needle is inserted coaxially into the lumen 15 of the catheter to form a catheter assembly 100. The combination is inserted under a patient's skin, typically into the patient's vein. The needle's tip 51 is ground to a sharp bevel to ease insertion into the patient. In accord with one implementation of the instant invention, the catheter is employed in conjunction with a needle 50 including a discontinuity 52. Such a discontinuity may be useful for, inter alia, allowing capture of the needle tip in a casing after use, thereby reducing incidents of inadvertent needle sticks, such as disclosed in U.S. Pat. No. 6,004,294 and U.S. application Ser. No. 09/717,148, filed Nov. 21, 2000, both incorporated herein by reference. Further, a notch 70 (see FIGS. 11 and 12) may be formed in the needle, proximal to the discontinuity, thereby creating a flash chamber of the central lumen 15 which provides a visual indication to a caregiver that he has successfully inserted the needle into a vein. Once in place in the patient, the needle is removed and the catheter remains, providing access through the lumen to the patient's blood stream. The proximal portion 12 of the catheter may be provided with various mechanisms, such as septums, luer locks, and the like, to provide selective access to the lumen (and, thereby, the patient's blood stream), as would be appreciated by one skilled in the art.

The catheter 1 formed in accord with the instant invention includes a predetermined internal geometry, defining the shape of the lumen 15 to improve operation of the over-the-needle catheter assembly 100. In particular, the catheter includes a catheter land 22 disposed at the distal portion 11 of the catheter at the tip 20, a proximal wall 24 (that is, the portion of the inner wall 14 at the proximal end of the catheter) and a shoulder 23 connecting the land to the proximal wall. These features each have predetermined shapes and dimensions, selected based on the particular intended implementation of the catheter. As currently preferred, the land has a circular cross-section with a constant diameter and a length equal to (or slightly less than) the needle tip length 53 (that is, referring to FIG. 3, the length of the needle 50 from the distal end of the discontinuity 52 to the beginning of the beveled tip 51 of the needle). As discussed below, the diameter of the land is preferably slightly less than the diameter of the needle near the tip such that there is a friction fit between the land and the needle. The proximal wall also has a predetermined length and, preferably, a circular cross-section. The shoulder 23 preferably has a conical shape, connecting the land with the proximal wall.

To form a catheter 1 in accord with one aspect of the instant invention, a tube 10 is formed of a flexible, biocompatible material, such as polytetrafluoroethylene (such as TEFLON®), polyvinyl chloride, polyethylene, polyurethane, polypropylene, or polyether urethane. The tube includes an inner wall 14 and an outer wall 13, each of which typically have substantially constant, circular cross-sections, thereby forming a straight tube. Preferably, the tube 10 is formed by extrusion or injection molding. The dimensions of the tube will vary depending on the application. For example, the inner wall 13 of the tube may have a diameter of 0.014 to 0.120 inches and the outer wall 14 may have an outer diameter of 0.020 to 0.140 inches. It will be appreciated by one skilled in the art that the tube may be manufactured using various techniques and will have dimensions appropriate for particular applications.

Figure 1:
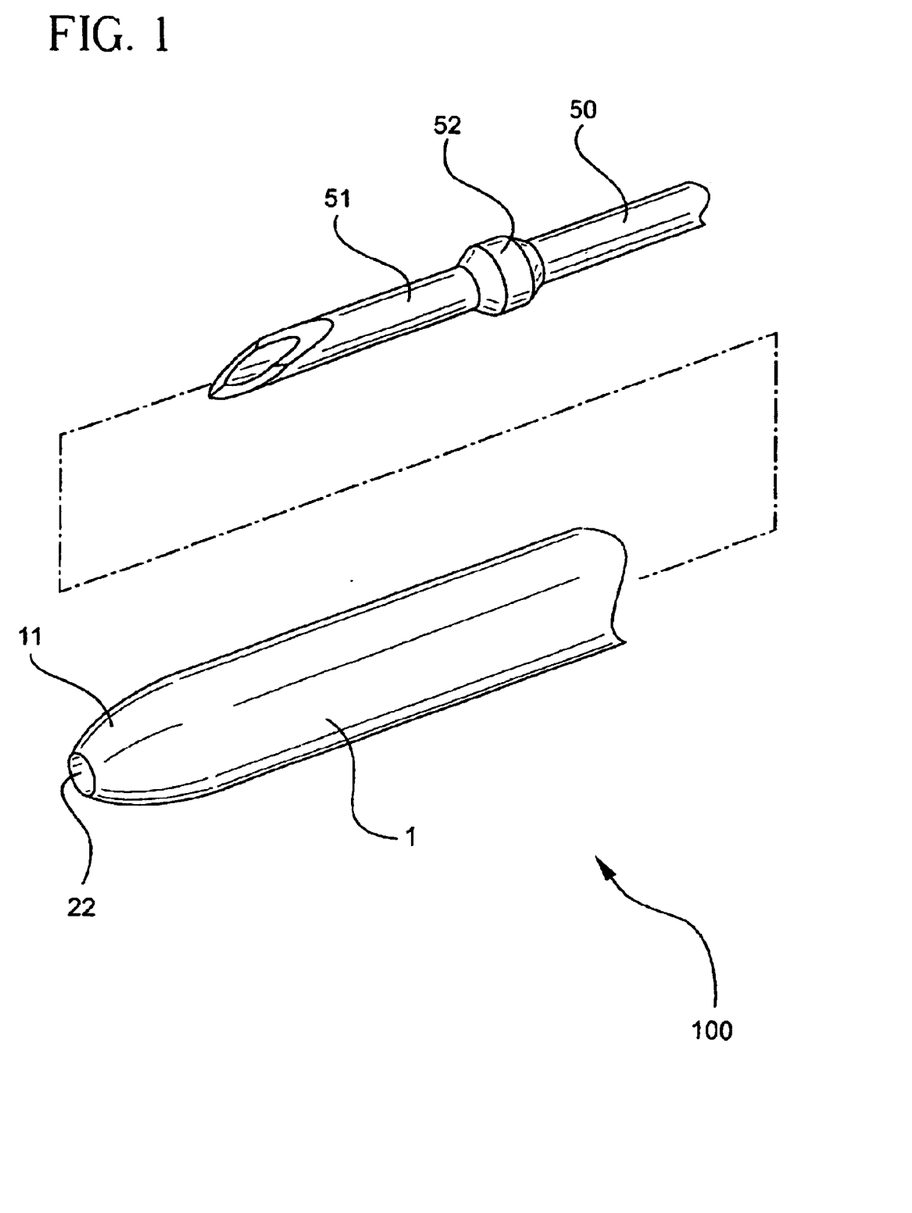
FIG. 1 is an exploded view of a catheter and needle assembly in accord with an aspect of the instant invention.
Figure 4A:
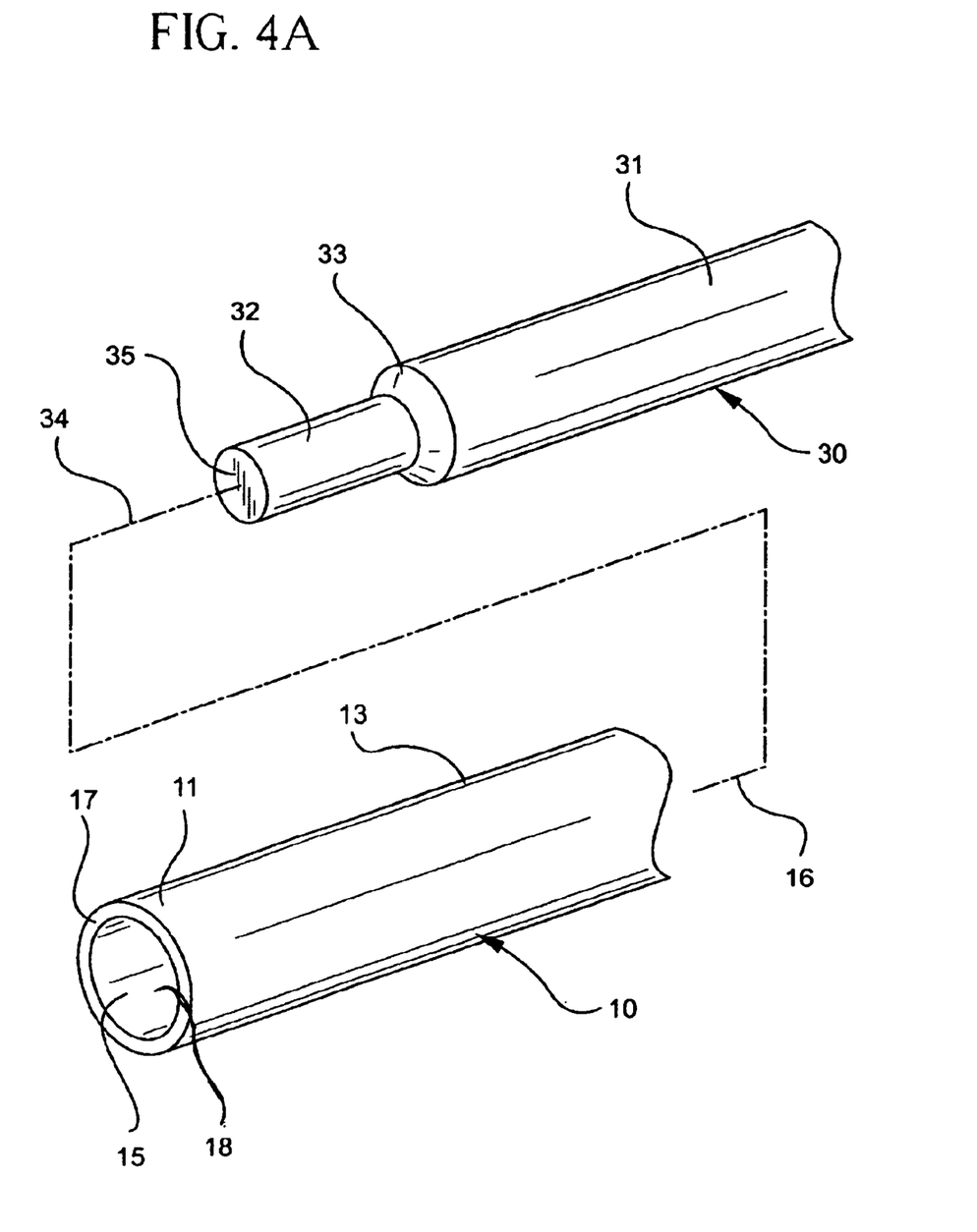
FIG. 4A is an expanded view of a mandrel being positioned in a tube in accord with an aspect of the instant invention.

A lumen 15 extends through the tube 10 and has a lumen axis 16. The tube itself has a distal portion 11 and a proximal portion 12. A distal face 17 of the tube is located remote from the proximal portion of the tube. As originally formed (and as depicted in FIG. 4A), the distal face 17 of the tube is in a plane perpendicular to the axis 16 of the tube. Consequently, a right angle is formed between the distal face and the outer wall 13. When passing through the patient's skin and into the vein, this right angle would contact the patient's skin, increasing the force required to insert the catheter and the discomfort felt by the patient. To reduce this force and discomfort, the catheter tip 20 is formed to a smooth bevel 21, such as depicted in FIGS. 1 and 4C, or other shapes known in the art.

The tip 20 of the catheter 1 is formed into a smooth bevel 21 using a mandrel 30 and a hot die 40. The mandrel includes a body portion 31 connected to the tip portion 32 by a ledge 33. Preferably, the mandrel is a surface of rotation formed about a mandrel axis 34. Most preferably, the body portion has a cylindrical shape with an outer diameter about equal to (or slightly less than) the diameter of the inner wall 14 of the tube 10 and the tip portion has a cylindrical shape with an outer diameter about equal to (or slightly less than) the outer diameter of the tip 51 of the needle 50 to be inserted into the formed catheter. Specifically, it is desirable that the outer diameter of the tip portion (and thus the internal diameter of the catheter land 22, discussed below) is slightly less than the outer diameter of the tip 51 of the needle 50 so that the catheter tip 20 has an interference fit on the needle tip. The interference fit is desirable so that when the over-the-needle catheter assembly 100 is taken out of its package, the catheter remains snugly on the needle and does not easily slip off. This interference fit also facilitates insertion of the over-the-needle catheter assembly into the patient's vein because it minimizes the chance that the catheter tip 20 will fold over or peel back on the needle tip 51, particularly in view of the structural support provided by the interaction of the discontinuity 52 and the shoulder 23. The specific dimensions of the mandrel will vary depending on the application intended for the catheter and the materials selected for the tube. For example, when the tube is made of PTFE, the tip portion of the mandrel is slightly larger than the desired final size of the catheter tip because the catheter will shrink somewhat during cooling. Certain materials do not shrink and thus the mandrel tip portion is sized slightly smaller than the tip of the needle.

Figure 4B:
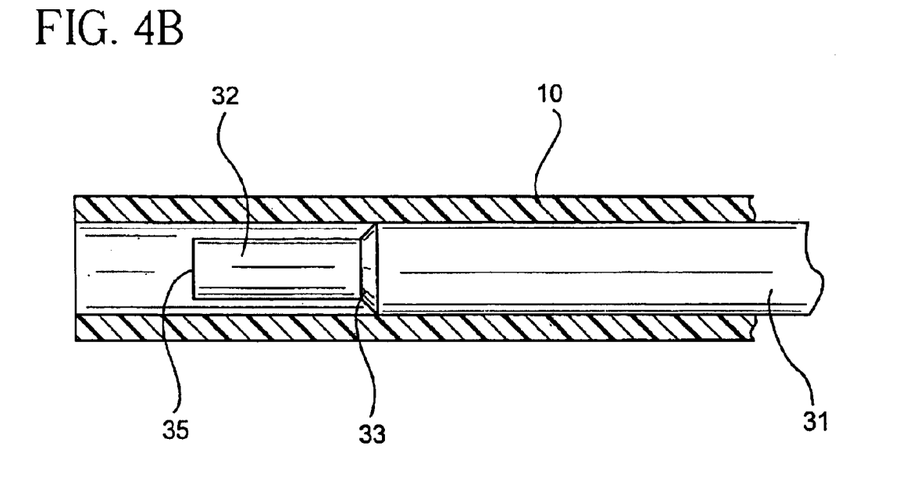
FIG. 4B is a partial cut-away view of the mandrel depicted in FIG. 4A seated within the tube.
Figure 4C:
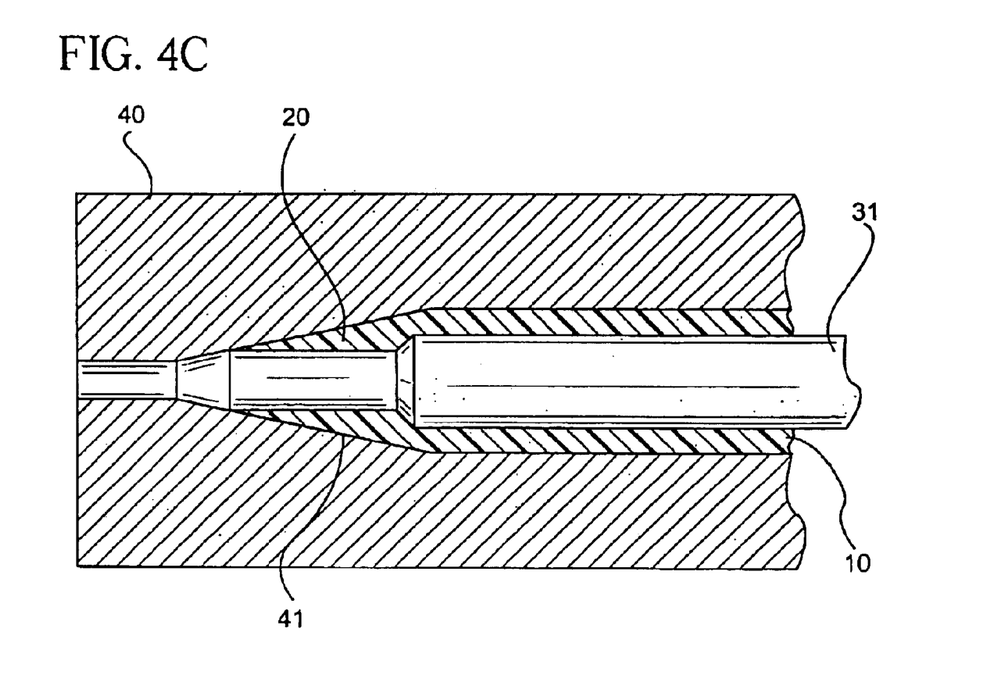
FIG. 4C is a partial cut-away view of the tube of FIG. 4B being deformed in a hot die.

As depicted in FIG. 4A, the ledge 33 of the mandrel 30 has an angled peripheral surface, forming an angle of about 4 degrees with the axis 34 of the mandrel (this nearly-perpendicular relationship between the axis and the ledge is exaggerated for clarity's sake in FIGS. 4A–4C). It will be appreciated that the ledge could be at other angles with respect to the axis of the mandrel. In particular, the ledge could be formed at a right angle with the axis of the mandrel, thereby forming a straight shoulder in the catheter, as discussed more fully below, or at a 45 degree angle with respect to the axis 34. Further, the ledge could also have other shapes, such as a convex or concave surface, as desired in a particular application of the invention. The ledge may also be formed asymmetrically about the mandrel axis such that the shoulder 23 formed in the catheter can engage the inserted needle 50 (or a feature 52 disposed thereon), preventing relative rotation, maintaining the catheter in a fixed orientation with respect to the needle.

Known catheter-tipping techniques, such as those disclosed in U.S. Pat. No. 4,661,300, incorporated herein by reference, may be used in connection with aspects of the instant invention. Other tipping techniques, such as those disclosed in U.S. Pat. Nos. 5,589,120; 5,736,085 and 5,843,356, each incorporated herein by reference, may also be employed in conjunction with aspects of the instant invention.

Referring now to FIGS. 4A through 4C, to form the catheter 1, the mandrel 30 is inserted into the lumen 15 of the tube 10. The mandrel proceeds through the lumen until the free end 35 of the tip portion 32 of the mandrel is near to the opening 18 in the distal face 17 of the tube. Preferably, the free end does not extend passed the opening. The tip portion of the mandrel and the distal portion of the tube are inserted into a hot die 40. Preferably, the tube is made of a thermoplastic material that deforms in the die. The very distal portion of the tube is cut off in the mandrel (the trimmings are not shown in FIG. 4C). The outer wall 13 of the tube contained within the die deforms to match the surface 41 of the die, creating a predetermined shape, such as the smooth bevel 21 depicted in FIG. 1. The inner wall 14 of the tube within the die deforms to conform to the surface of the mandrel, such that the tube has a shoulder 23 formed at the ledge 33 of the mandrel and a catheter land 22 formed at the tip portion 32 of the mandrel. Once formed, the catheter is cured by cooling. The mandrel or die may be cooled, cool air may be delivered to the catheter or cooling provided by other techniques. As will be appreciated, formed in this manner, the catheter land and the shoulder will have a predetermined shape defined by the shape of the mandrel.

Once the tube 10 has been formed into the catheter 1, the catheter is removed from the die and the mandrel is removed from the lumen 15. A needle 50 is inserted into the lumen such that the tip 51 of the needle extends beyond the tip 20 of the catheter. In one particularly advantageous application of the instant invention, the needle is provided with a discontinuity 52, such as a bump or ledge formed on the exterior of the needle or attached to the exterior of the needle. The length of the catheter land 22 is selected such that the distal face or edge 54 of the discontinuity abuts the shoulder 23 in the catheter when the needle is positioned as desired in the lumen of the catheter. Typically, it is preferably that the entire bevel of the tip 51 of the needle extend beyond the catheter tip 21. Consequently, land 22 should be of a length less than the distance 53 between the distal face of the discontinuity and the proximal portion of the needle tip. During inserting into the patient's vein or a septum located within the patient's body (such as employed with an implantable infusion port), the engagement of the shoulder with the discontinuity on the needle prevents the catheter from rolling up the needle (that is, folding back or collapsing proximally along the needle length). When the needle and catheter are in place, the needle can simply be withdrawn. The shoulder does not interfere with the movement of the needle in the proximal direction.

The cross-section of the proximal wall 24 is selected to permit movement of the discontinuity 52 therethrough. The cross-section of the land is selected to prevent movement of the discontinuity therethrough, but to permit passage of the needle tip 51. Preferably, the cross-section of the land is selected such that the needle tip sits snugly within the land, such as depicted in FIG. 3. The land 22 may be shaped to mate with the distal face of the discontinuity while permitting fabrication of the catheter without difficulty.

Figure 5A:
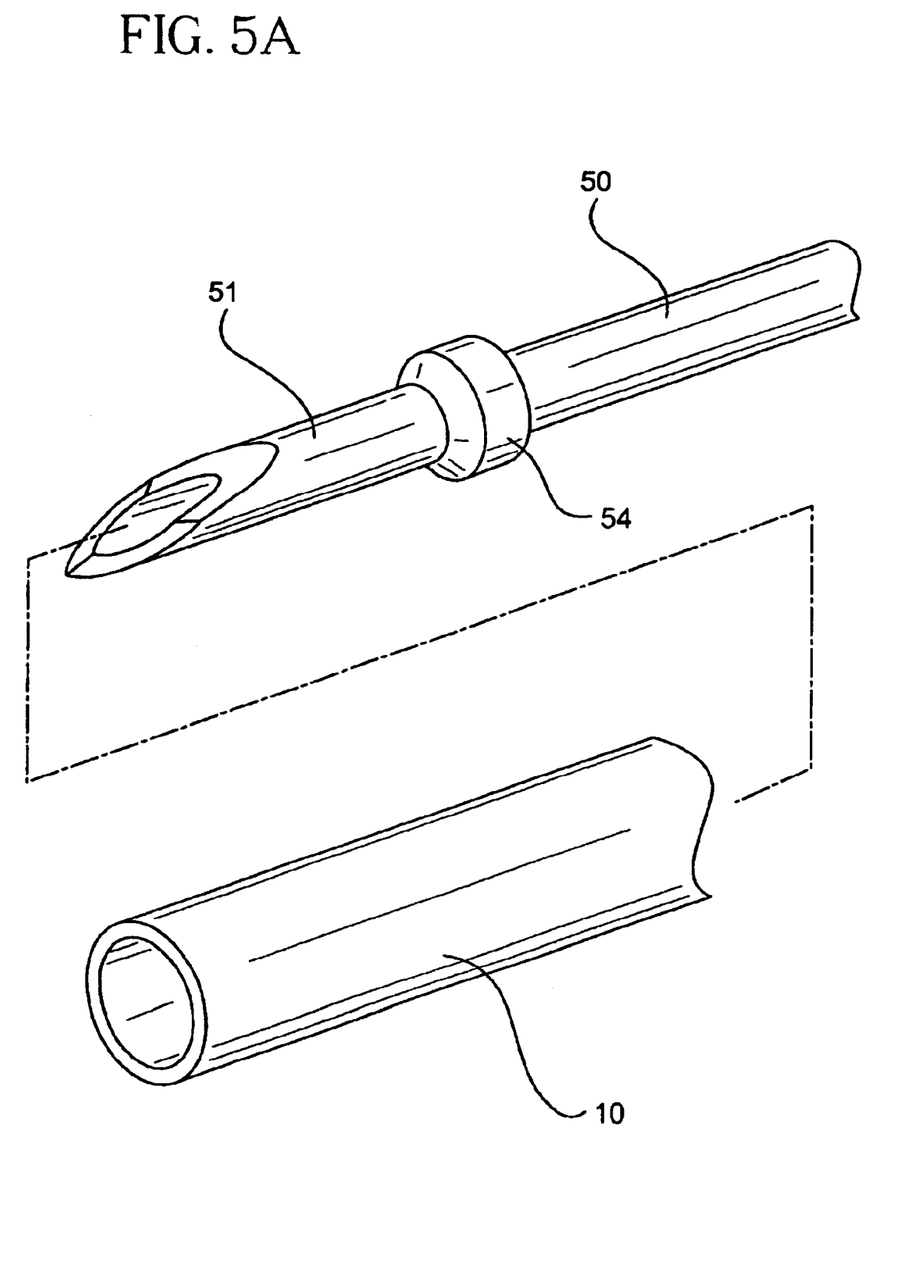
FIG. 5A is an expanded view of a needle being positioned in a tube in accord with another aspect of the instant invention.
Figure 5B:
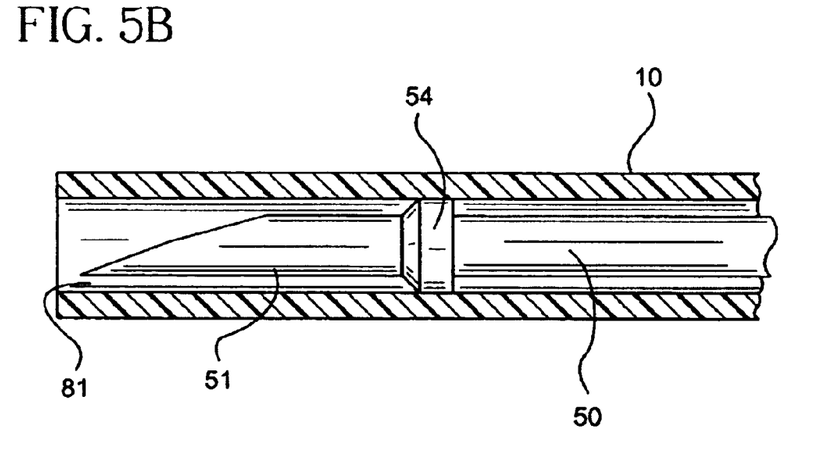
FIG. 5B is a partial cut-away view of the needle depicted in FIG. 5A seated within the tube.
Figure 5C:
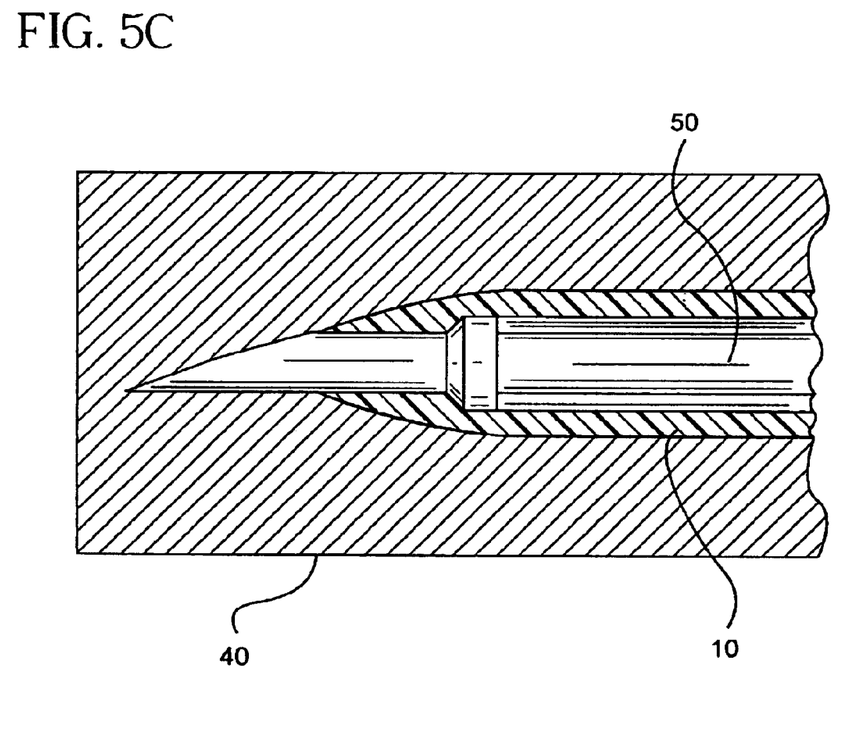
FIG. 5C is a partial cut-away view of the tube of FIG. 5B being deformed in a hot die in which the needle is serving as a mandrel.

Referring to FIGS. 5A through 5C, the needle 50 itself may be employed as a mandrel 30. The tipping process as discussed in connection with FIGS. 4A–4C may also be employed when the needle serves as the mandrel. Alternatively, the needle may be positioned within the lumen 15 of the tube 10 such that the beveled tip 51 of the needle extends out of the opening 18 at the distal portion of the tube. The needle/tube combination is then inserted into a hot die 40. The discontinuity 52 on the needle serves as a ledge 33 and the shoulder 23 in the catheter 1 is formed directly onto the discontinuity, creating an over-the-needle assembly 100.

Figure 11:
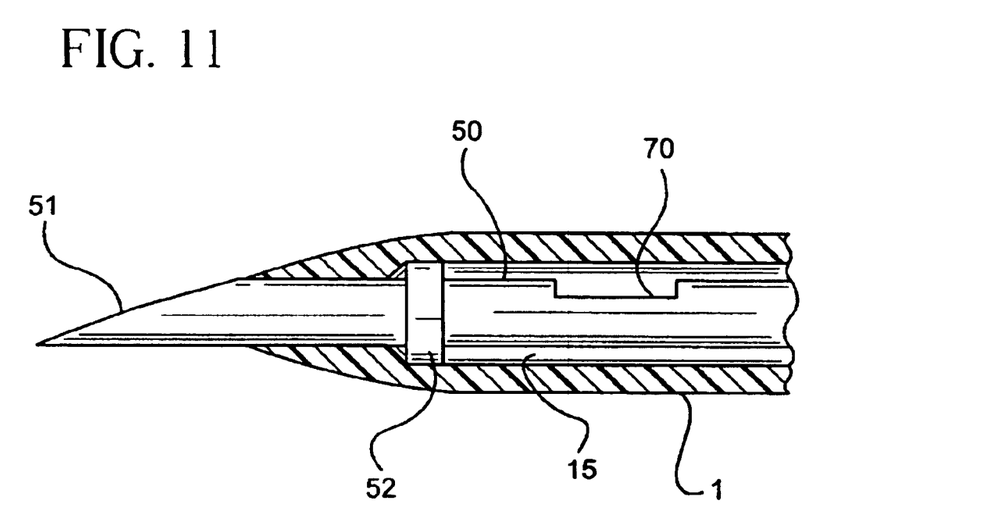
FIG. 11 is a cut-away side view of a catheter formed in accord with an aspect of the invention shown mounted to a needle.
Figure 12:
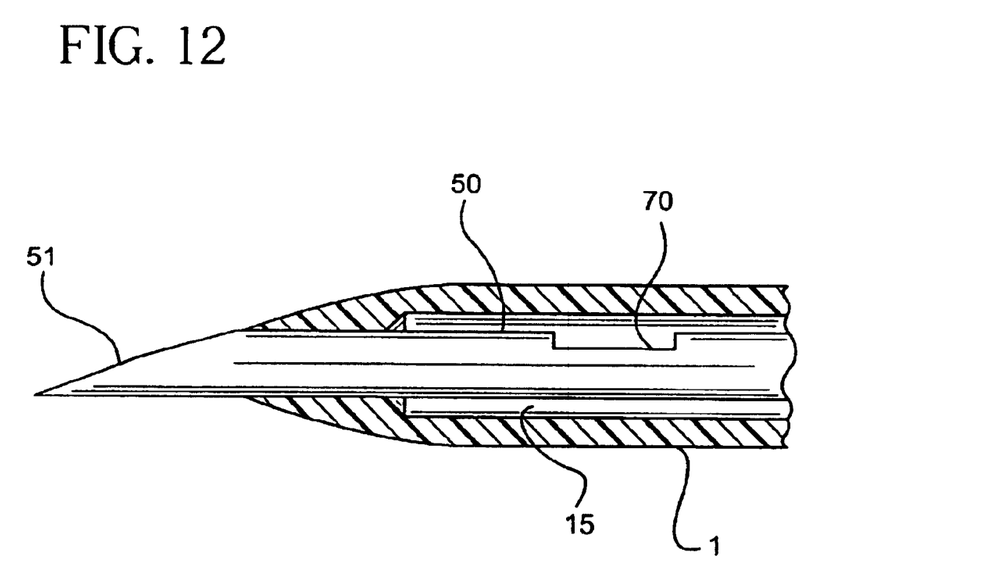
FIG. 12 is a cut-away side view of a catheter formed in accord with an aspect of the invention mounted to a needle with no discontinuity.

It will be appreciated that the discontinuity 52 may have various shapes and be formed in various manners. For example, the discontinuity may be formed by a crimp or notch in the needle. Alternatively, a shoulder may be ground into the needle wall to serve as a discontinuity. Further, an annular ring may be attached to the needle to form the discontinuity. The discontinuity may have a beveled proximal face and distal face as shown in FIG. 4, a beveled proximal face and a straight distal face as shown in FIG. 5A, or two straight faces as shown in FIG. 11. Other shapes may be employed and still practice aspects of the invention. Indeed, aspects of the invention may be employed with needles that do not have a discontinuity (see FIG. 12).

After it is tipped, the catheter 1 and its tip 20 are preferably free of defects (such as incomplete formation, substantial flash, rollovers or jagged edges) and look smooth. A lubricant is used to allow the tipped catheter 1 to be easily removed from the mandrel 30 and die 40 without creating such a defect or stretching the formed catheter. The tipping lubricant may be a polydimethyl siloxane such as Dow Corning DC 360 or curable silicones such as Dow Corning 44159 MDX, which are amine terminated and moisture curable. Non-curable amine terminated polydimethyl siloxanes have also been used for this purpose. Such lubricants are described in, for example, U.S. Pat. Nos. 3,574,673; 4,904,433; and 5,185,006, all incorporated herein by reference. The amount of lubricant needed to provide adequate lubricity between the catheter and the mandrel and die is very small. The catheter may be dipped into a solution including the lubricant, thereby facilitating application of the lubricant to the inner wall 14 and the outer wall 13 of the tube before forming on the mandrel and die. The silicone oils used as typical lubricants are hydrophobic. Therefore, these compounds must be dissolved in solvents, as would be appreciated by one skilled in the art, in order to prepare a solution in which the catheter tip can be dipped for lubrication before tipping can begin.

It is currently preferred that the tube 10 be made of a thermoplastic material which is formed into the catheter 1 in the hot die 40. However, the mandrel 30 itself could be heated (either alone or in combination with the die) to deform the tube. Further, other plastic or polymeric materials may be employed to form the tube. If appropriate, these materials can be cured to maintain the shape formed by the mandrel and the die. For example, certain materials can be forced into the die, compressed into a shape matching the die and the mandrel, and cured to maintain that shape after removal of the die and the mandrel. Thermoset materials, such as silicone and rubber, may be injected into a mold and cured with heat. Other such materials having various such properties may be employed and practice aspects of the invention.

It will be appreciated that the proximal wall 24, the land 22 and the shoulder 23 may have different shapes and dimensions and still practice aspects of the invention. For example, the length of the land may be selected such that a substantial portion of the needle tip 51 extends out of the catheter tip 20. Conversely, the land length may be selected such that only a portion of the needle tip extends out of the catheter tip, or that the needle tip be completely enveloped within the catheter tip. In such case, the catheter may operate as a protective sleeve that needs to be removed before use. The cross-section of the land may also be selected so that it is smaller than the needle tip, thereby forming a tight fit with the needle tip and preventing any relative sliding until desired by the caregiver. The cross-section of the land may be an oval or other shape having a dimension less than the diameter of the needle tip, again creating a snug fit with the needle tip. Further, the land may be provided with features such as tabs or ribs to create a structural relationship between the land and the tip as desired in any particular application of the instant invention. Such features allow control of the friction between the tip and the land, the flexibility of the external surface of the catheter tip, and other characteristics of the over-the-needle catheter assembly.

Referring to FIG. 11, a notch 70 may be positioned in the needle 50 distal to the discontinuity 52. The notch creates a passageway between the central axial cavity of the needle and the lumen 15 of the catheter 1. When the needle tip is inserted into the patient's vein, blood proceeds through the interior chamber of the needle, through the notch and within the lumen, at least up to the discontinuity. The blood in the lumen is visible to the caregiver. Consequently, the catheter and notch operate as a flash chamber, providing visual indication for a caregiver that she has successfully accessed the patient's vein.

The shoulder 23 may also have various shapes and dimensions as desired to achieve characteristics desired in a particular application. As discussed above, the shoulder may be shaped to match the distal surface or edge 54 of the discontinuity 52. As seen in FIG. 3, the shoulder has a conical shape to match the bevel on the discontinuity. The shoulder may also be formed at a right angle with respect to the axis of the catheter if the discontinuity has a flat, perpendicular distal surface. Alternatively, the shoulder could be formed with ridges and the like to control the release force required to remove the needle from the catheter. If the ridges match ridges on the distal surface of the discontinuity, the release force may be increased. If the distal surface is smooth, the ridges may decrease the release force.

The proximal wall may also be formed with a predetermined geometry to achieve particular performance characteristics. For example, ridges and tabs may be formed in the proximal wall, which engage the discontinuity as the needle is removed. The ridges may be sized to increase or decrease the removal force required to remove the needle. It will be appreciated that, employing the instant invention, various predetermined geometries may be employed for the proximal wall 24, the shoulder 23 and the catheter land 22 to achieve distinct performance characteristics.

Figure 6A:
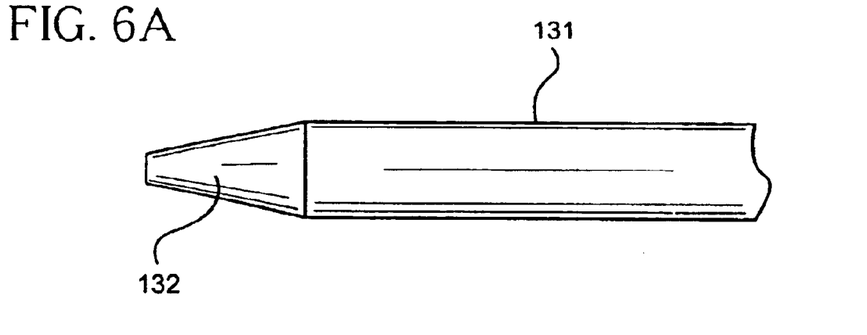
FIGS. 6A and 6B are front and side elevation views, respectively, of a mandrel for use in connection with one aspect of this invention.
Figure 6B:
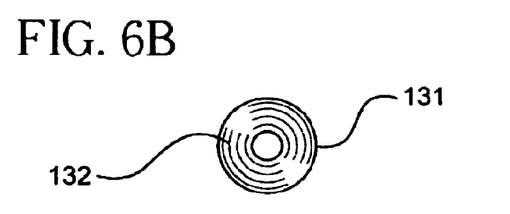

Referring to FIGS. 6A and 6B through FIGS. 10A and 10B, various mandrels adapted to be used with the instant invention are depicted. In FIGS. 6A and 6B, the body portion 131 of the mandrel has a cylindrical shape while the tip portion 132 has a conical shape, narrowing toward the free end 135. A catheter formed by this mandrel will include a catheter land 22 at the opening 18.

Figure 7A:
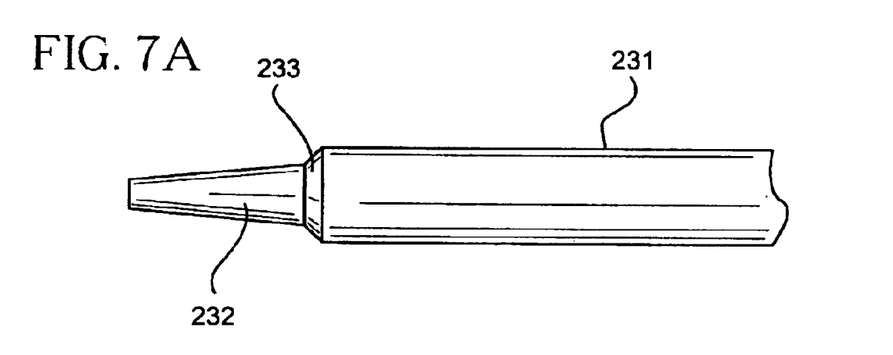
FIGS. 7A and 7B are front and side elevation views, respectively, of a mandrel for use in connection with another aspect of this invention.
Figure 7B:
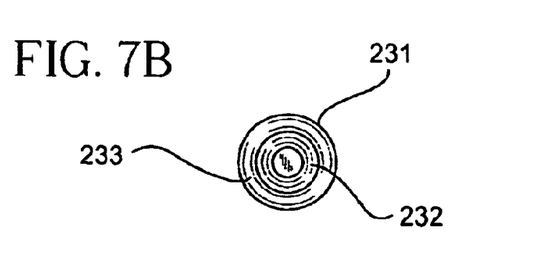

The mandrel in FIGS. 7A and 7B includes a cylindrical body portion 231, a conical ledge 233 and a conical tip portion 232. Use of this mandrel will produce a catheter with a two-stage conical lumen. As depicted, the tip portion is formed at a steeper angle than the ledge. It will be appreciated that the ledge could be formed at a steeper angle than the tip portion, or at a matching angle, and still practice the invention.

Figure 8A:
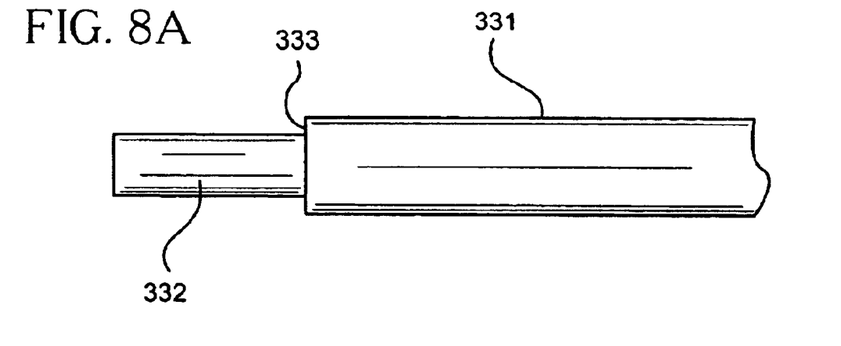
FIGS. 8A and 8B are front and side elevation views, respectively, of a mandrel for use in connection with yet another aspect of this invention.
Figure 8B:
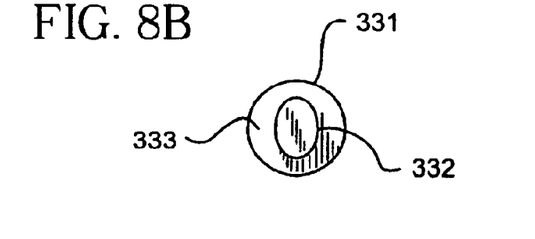
Figure 9A:
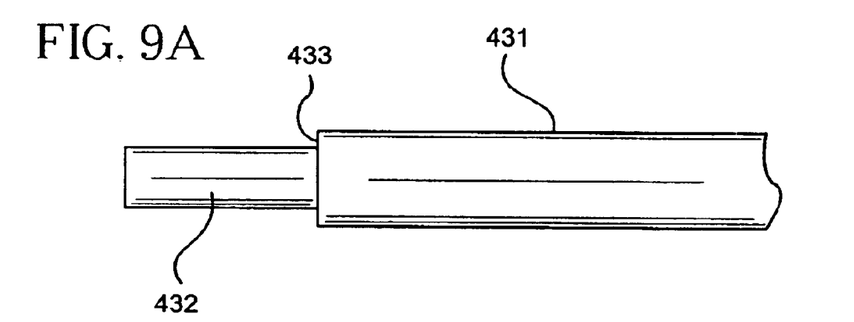
FIGS. 9A and 9B are front and side elevation views, respectively, of a mandrel for use in connection with yet another aspect of this invention.
Figure 9B:
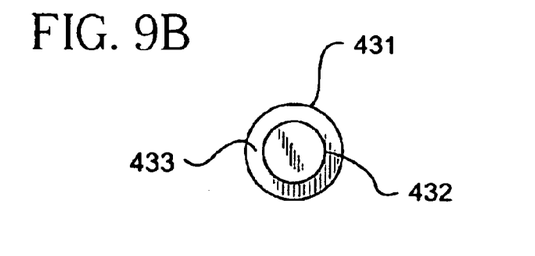

The mandrel depicted in FIGS. 8A and 8B includes a cylindrical body portion 331 with a tip portion 332 having an oval cross-section connected by a ledge 333 perpendicular to the axis of the mandrel. The mandrel depicted in FIGS. 9A and 9B includes a cylindrical body portion 331 with a tip portion 332 having a circular cross-section connected by a ledge 333 perpendicular to the axis of the mandrel. For certain applications, the formation of a right angle shoulder, such as that formed by these mandrels, may be advantageous.

Figure 10A:
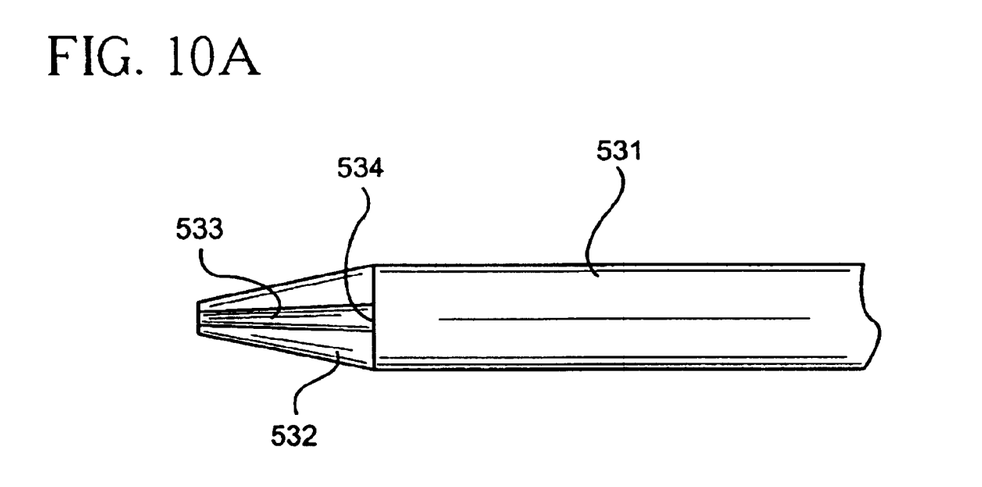
FIGS. 10A and 10B are front and side elevation views, respectively, of a mandrel for use in connection with yet another aspect of this invention.
Figure 10B:
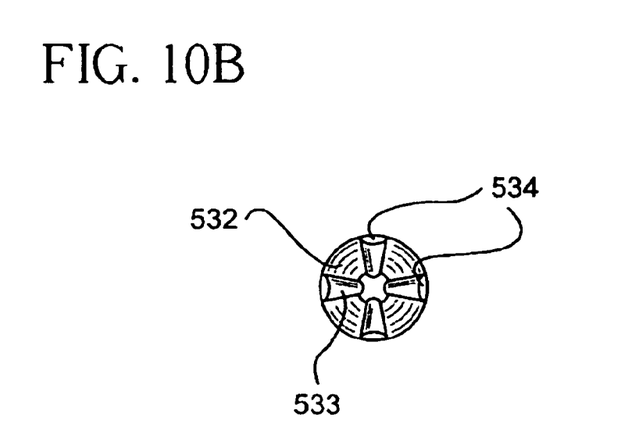

The mandrel depicted in FIGS. 10A and 10B includes a body portion 531 and a tip portion 532 with a groove 533 extending therethrough. Shoulders 534 are formed at the junction of the body portion and the tip portion. This mandrel would produce a catheter having ribs extending axially through the lumen at the distal end of the catheter.

Although the invention is described herein in connection with a typical peripheral IV catheter employed in an over-the-needle assembly, it is understood that the invention is applicable to other catheters and deformable tubing employed for medical purposes, such as introducers and the like. For example, this invention is applicable to extended dwell catheters and other medical devices in which it is desired to employ catheters having predetermined internal and external geometry. In addition, while this invention is satisfied by embodiments in many different forms, preferred embodiments of the invention are shown in the drawings and described in detail herein. The scope of the invention is measured by the appended claims.

We claim:

1. A method of forming a catheter for use with a needle having a tip and a discontinuity, the discontinuity having a cross-section, the method including:

extruding a flexible, bio-compatible, thermoplastic material into a tube, the tube having an inner wall defining a substantially constant inner cross-section, an outer wall defining a substantially constant outer cross-section, a proximal portion, a distal portion, a distal face on the distal portion remote from the proximal portion, and an axis;

wherein a lumen is defined by the inner wall and extends co-axially within the tube from the proximal portion, through the distal portion to the distal face, forming an opening in the distal face;

providing a mandrel with a body portion having a cross-section, a tip portion having a cross-section, and a ledge disposed between the body portion and the tip portion, wherein the cross-section of the body portion is larger than the cross-section of the tip portion;

inserting the mandrel into the lumen such that the tip portion of the mandrel is disposed in the distal portion of the tube proximate to the distal face of the tube;

placing the distal portion of the tube in a heated die;

heating the distal portion of the tube such that the outer wall is deformed to taper inward toward the opening and the inner wall is deformed to conform to the tip portion of the mandrel;

forming a catheter land having a predetermined cross-section substantially matching the cross-section of the tip portion and a predetermined length, wherein the cross section of the catheter land is smaller than the cross section of the discontinuity on the needle; and withdrawing the mandrel from the lumen.

2. The method of claim 1 wherein the mandrel is coated with polytetrafluoroethylene.

3. The method of claim 1 wherein the body portion of the mandrel has a cylindrical shape, the tip portion of the mandrel has a cylindrical shape and the ledge has a conical shape.

4. The method of claim 3 further comprising inserting the needle into the lumen after withdrawing the mandrel, wherein the inner wall has a diameter that is less than the diameter of the needle.

5. The method of claim 4 wherein the discontinuity on the needle is positioned a fixed distance from a tip of the needle and the predetermined length of the catheter land is determined based, at least in part, on the fixed distance.

6. A method of forming a catheter for insertion into a patient, including:

extruding a flexible, bio-compatible material into a tube, the tube having an inner wall, an outer wall, a proximal portion, a distal portion, a distal face on the distal portion remote from the proximal portion, and an axis, wherein a lumen is defined by the inner wall and extends co-axially within the tube from the proximal portion, through the distal portion to the distal face, forming an opening in the distal face;

providing a mandrel with a body portion and a tip portion, each having a cross section, wherein the cross-section of the body portion is larger than the cross-section of the tip portion, and wherein the cross-section of the tip portion is less than the inner cross-section of the tube;

inserting the mandrel into the lumen such that the tip portion of the mandrel is disposed in the distal portion of the tube near the distal face of the tube;

deforming the distal portion of the tube such that the outer wall tapers inward toward the opening; and deforming the lumen at the distal portion to conform to the tip portion of the mandrel, thereby forming a catheter land having a predetermined length and a predetermined cross-section substantially matching the cross-section of the tip portion.

7. The method of claim 6 wherein the material of the tube is thermoplastic, and wherein the step of deforming the distal portion of the tube includes heating the distal portion such that it conforms to the mandrel.

8. The method of claim 7 wherein the distal portion of the tube is heated in a hot die which substantially surrounds the distal portion.

9. The method of claim 7 wherein the mandrel is heated to deform the distal portion.

10. The method of claim 8 wherein the mandrel is heated to deform the distal portion.

11. The method of claim 6 further including curing the tube after it has been deformed.

12. The method of claim 6 wherein the mandrel has a free end at the tip portion, distal to the body portion, and wherein, when the mandrel is inserted into the lumen, the free end is co-located with the distal end of the tube.

13. The method of claim 6 wherein the mandrel has a free end at the tip portion, distal to the body portion, and wherein, when the mandrel is inserted into the lumen, the free end extends out of the lumen.

14. The method of claim 6 wherein the mandrel has at least one ledge disposed between the body portion and the tip portion, further comprising deforming the tube such that at least one shoulder is formed in the tube about the ledge.

15. The method of claim 6 wherein the distal end of the tube is deformed by compression in a mold.

16. The method of claim 6 wherein the mandrel is a needle for insertion through a patient's skin.

17. The method of claim 6 wherein the predetermined length of the catheter land is determined based, at least in part, on the distance between a tip of a needle and a discontinuity on the needle.

18. The method of claim 6 wherein the cross section of the tip portion is the same or less than the cross section of a needle and less than the cross section of a discontinuity on the needle.

19. A method of forming a catheter for insertion into a patient's skin, including:

extruding a flexible, bio-compatible material into a tube, the tube having an inner wall defining a substantially constant inner cross-section, an outer wall defining a substantially constant outer cross-section, a proximal portion, a distal portion, a distal face on the distal portion remote from the proximal portion, and an axis, wherein a lumen is defined by the inner wall and extends co-axially within the tube from the proximal portion, through the distal portion to the distal end, forming an opening in the distal face;

providing a mandrel with a body portion, a tip portion, a ledge connecting the body portion to the tip portion, and a free end disposed on the tip portion remote from the body portion;

inserting the mandrel into the lumen such that at least the free end of the tip portion of the mandrel passes through the opening and is disposed out of the lumen;

deforming the distal portion of the tube such that the outer wall tapers inward toward the opening; and deforming the lumen at the distal portion to conform to the tip portion of the mandrel, thereby forming a catheter land having a predetermined cross-section substantially matching a cross-section of the tip portion and a predetermined length.

20. The method of claim 19 wherein the tip portion of the mandrel has a conical shape, narrowing toward the free end.

21. The method of claim 20 wherein the ledge has a conical shape.

22. The method of claim 21 wherein the conical shape of the ledge matches the conical shape of a shoulder formed in the tube.

23. The method of claim 19 wherein the tip portion of the mandrel has an oval cross-section.

24. The method of claim 19 wherein the tip portion of the mandrel has a cylindrical shape, the body portion of the mandrel has a cylindrical shape, and the ledge is perpendicular to the axis of the tube when the mandrel is disposed in the lumen.

25. The method of claim 19 wherein the tip portion of the mandrel has grooves extending from the ledge to the free end.

* * * * *